(12) United States Patent
Bauer et al.

(10) Patent No.: US 10,172,954 B2
(45) Date of Patent: Jan. 8, 2019

(54) USE OF A REVERSE-MICELLAR SYSTEM FOR DELIVERING CHELATORS OF RADIONUCLIDES AND METALS

(71) Applicant: MEDESIS PHARMA, Baillargues (FR)

(72) Inventors: Caroline Bauer, Rochefort du Gard (FR); Elsa Compte, Montpellier (FR); Olivier Gremy, Saint Germain les Arpajon (FR); Laurent Miccoli, Juvisy sur Orge (FR); Jaime Francisco Angulo-Mora, Limours (FR); Jean-Claude Maurel, Castries (FR)

(73) Assignee: MEDESIS PHARMA, Baillargues (FR)

( * ) Notice: Subject to any disclaimer, the term of this patent is extended or adjusted under 35 U.S.C. 154(b) by 0 days.

(21) Appl. No.: 15/119,678

(22) PCT Filed: Feb. 17, 2015

(86) PCT No.: PCT/EP2015/053339
§ 371 (c)(1),
(2) Date: Aug. 17, 2016

(87) PCT Pub. No.: WO2015/124581
PCT Pub. Date: Aug. 27, 2015

(65) Prior Publication Data
US 2017/0035909 A1 Feb. 9, 2017

(30) Foreign Application Priority Data

Feb. 18, 2014 (EP) .................................... 14305217

(51) Int. Cl.

| A61K 47/69 | (2017.01) |
|---|---|
| A61K 47/48 | (2006.01) |
| A61K 49/10 | (2006.01) |
| A61K 49/18 | (2006.01) |
| A61K 9/00 | (2006.01) |
| A61K 47/54 | (2017.01) |

(52) U.S. Cl.
CPC ........ *A61K 47/48807* (2013.01); *A61K 9/006* (2013.01); *A61K 47/547* (2017.08); *A61K 47/6909* (2017.08); *A61K 49/103* (2013.01); *A61K 49/1809* (2013.01)

(58) Field of Classification Search
None
See application file for complete search history.

(56) References Cited

U.S. PATENT DOCUMENTS

| 5,807,527 | A * | 9/1998 | Burgoyne | ................ C12Q 1/68 424/488 |
|---|---|---|---|---|
| 7,361,275 | B2 * | 4/2008 | Wien | ...................... C02F 1/004 210/638 |
| 2008/0015263 | A1 | 1/2008 | Bolotin et al. | |
| 2013/0251815 | A1 | 9/2013 | Talton | |

FOREIGN PATENT DOCUMENTS

| WO | WO-2005/089412 A2 | 9/2005 |
|---|---|---|
| WO | WO-2011/117333 A2 | 9/2011 |
| WO | WO-2011/117334 A2 | 9/2011 |

OTHER PUBLICATIONS

Defintion of Sequestering Agent from https://www.corrosionpedia.com/definition/1022/sequesteringagent, accessed Sep. 13, 2017.*
Abdelkader Mouri et al., "Phase behavior of reverse microemulsions based on Peceol," Journal of Colloid and Interface Science, vol. 416, Feb. 2014, pp. 139-145.
Jospeh D. Reddy et al., "Preclinical Toxicology, Pharmacology, and Efficacy of a Novel Orally Administered Diethylenetriaminepentaacetic acid (DTPA) Formulation," Drug Development Research, vol. 73, 2012, pp. 232-242.
International Search Report and Written Opinion issued in International Patent Application No. PCT/EP2015/053339 dated May 20, 2015.

* cited by examiner

Primary Examiner — Nissa M Westerberg
(74) Attorney, Agent, or Firm — Arent Fox LLP (57) ABSTRACT

The present invention relates to reverse-micellar systems comprising at least an active agent, an acylglycerol, a sterol, lecithin, ethanol and water, for use in chelation and/or sequestering of a radionuclide and/or a metal in a patient. The invention also relates to the reverse-micellar systems and to pharmaceutical compositions comprising said reverse-micellar systems.

5 Claims, 3 Drawing Sheets

USE OF A REVERSE-MICELLAR SYSTEM FOR DELIVERING CHELATORS OF RADIONUCLIDES AND METALS

CROSS REFERENCE TO RELATED APPLICATION

This application is a 35 U.S.C. 371 National Phase of PCT Application No. PCT/EP2015/053339 filed Feb. 17, 2015, which claims priority to European Patent Application No. 14305217.3 filed Feb. 18, 2014, the disclosure of which is hereby incorporated in its entirety by reference.

INTRODUCTION

The present invention relates to reverse-micellar systems comprising at least an active agent, an acylglycerol, a sterol, lecithin, ethanol and water, for use in chelation and/or sequestering of a radionuclide and/or a metal in a patient. The invention also relates to the reverse-micellar systems and to pharmaceutical compositions comprising said reverse-micellar systems.

BACKGROUND OF THE INVENTION

Exposure to radionuclides may have different origins, from the involvement of a nuclear worker after breaking of the containment of a glove box for example, to that of a multitude of people contaminated by the widespread dissemination of radionuclides in the environment: incident/accident or natural disaster affecting facilities of research, production, operation or storage of nuclear materials, military conflict with nuclear weapons, radionuclide containing weapons, terrorist act aiming at these facilities or characterized by an explosive device dispersing radionuclides called "dirty bomb."

Internalized radionuclides are highly toxic and may cause both acute and chronic radiation injuries. The nuclides the most frequently encountered in these scenarios include americium, cesium, iodine, plutonium, strontium, uranium. Plutonium (Pu) is an example of highly toxic transuranic actinide alpha emitter. Once internalized in the body, Pu is overwhelmingly and efficiently distributed between the primary site of infection (e.g. the lungs in the case of inhalation) and the two main secondary tissue deposits (bone and liver), for very long periods.

To reduce the cumulative radiation dose delivered to the tissues by the Pu atoms, and thus reduce the risk of developing diseases, the only possibility is their decorporation by chelation to facilitate their excretion by natural means.

Currently, the only recommended treatment for actinide/lanthanide decorporation, such as Pu decorporation, is chelator diethylene triaminopentaacetic acid (DTPA), which in its dosage form solution benefits from a marketing authorization in France (2008), Germany (2005) and the approval of the Food and Drug Administration USA (2004). The marketed DTPA solution can be injected or infused intravenously, applied on a contaminated wound, or nebulized for inhalation.

DTPA is highly polar at neutral pH and is thus poorly (<10%) or variably absorbed when delivered orally. Consequently, DTPA is generally administered through more invasive routes, such as intravenous injection for internal contamination routes. Intravenous administration requires medical assistance and can thus not be autonomously used by any contaminated person.

Nebulization administration and flush of a contaminated wound are local and not optimal administration routes for decorporation efficacy in patients and do not necessarily afford systemic delivery. Wound flushing with a solution comprising DTPA triggers spilling of contaminated DTPA solution and waste of a great quantity of DTPA.

Reddy et al. Drug Development Research 2012, 73, 232-242 and US 2013/0251815 disclose enteric-coated gelatin capsules encapsulating DTPA that are safe and capable of decorporating actinides. Said capsules can be administered orally.

Jay et al. U.S. Pat. No. 8,030,358 and WO 2013/109323 disclose oral and topical delivery of DTPA prodrug formulations respectively.

However, there still exists a real need of new formulations, which would allow simple and autonomous (i.e. without medical assistance) administration of decorporating agents, such as DTPA. Such formulations would be especially appropriate for large-scale treatment of contaminated people and chronic treatments. In addition, most described systems for oral or local delivery require the use of high doses of DTPA, because these routes do not favor the uptake of the active agent.

Metal poisoning is a serious health problem. It can occur in different contexts, and potentially involves a wide variety of metals. Metal can also be present in too high U.S. Pat. No. 5,494,935 discloses the use of compositions comprising partially lipophilic polyaminocarboxylic acids, for chelating heavy metals in specific organs in the body. These compositions are in particular capable of oral administration.

The described formulations for oral delivery of decontaminating agents or of agents for treating metal intoxication often require high doses, may be toxic and are usually not as efficient as the corresponding formulations for intravenous administration.

WO 2011/117333 discloses the use of a reverse-micellar system based on acylglycerols, phospholipids or sphingolipids and metal ions. Said reverse micellar systems are able to cross mucosa and cellular membranes and thus allow vectorization of metal ions to target sites. The reverse-micellar system allows the delivery of the metal ions to many different organs.

The Applicant surprisingly evidenced that reverse-micellar systems based on acylglycerols, sterols, lecithin, ethanol, water and a chelating or sequestering agent are appropriate for efficient chelation of radionuclides and/or metals in the whole body. Said reverse-micellar system can be advantageously delivered by transmucosal route, and favour the delivery and/or absorption of the active agent into the desired cells or organs. The reverse-micellar system acts both as a protecting shell around the active agent, and as a vector for its delivery to the desired cells and/or organs.

SUMMARY OF THE INVENTION

The first object of the invention is a reverse-micellar system comprising at least an active agent, an acylglycerol, a sterol, lecithin, ethanol and water, for use in chelation and/or sequestering of a radionuclide and/or a metal, in a patient in need thereof.

Another object of the invention is a reverse-micellar system comprising at least an active agent, an acylglycerol, a sterol, lecithin, ethanol and water, wherein the active agent is selected from the group consisting of DTPA, bisphosphonates, Prussian blue, EDTA (ethylene diamine tetraacetic acid), Trientine, D-penicillamine, Deferoxamine, BAL (British Anti-Lewisite), DMSA (DiMercaptoSuccinic Acid), DMPS (2,3-DiMercaptoPropane-1-Sulfonic acid), Phytic acid, hydroxypyridonates (HOPO), mercaptoacetyltriglycine (MAG3) or chelating peptides, or derivatives thereof and combinations thereof.

Another object of the present invention is a reverse-micellar system comprising at least an active agent, an acylglycerol, a sterol, lecithin, ethanol, water, and at least one radionuclide and/or metal, wherein the active agent is a compound appropriate for chelating and/or sequestering said radionuclide and/or metal.

Another object of the invention is a reverse-micellar system comprising at least an active agent, an acylglycerol, a sterol, lecithin, ethanol, water and a radionuclide and/or metal, wherein the active agent is a compound appropriate for chelating and/or sequestering said radionuclide and/or metal, for use as an imaging agent and/or as a diagnosis agent.

Another object of the invention is a pharmaceutical composition comprising a pharmaceutically acceptable support and a reverse-micellar system comprising at least an active agent, an acylglycerol, lecithin, ethanol and water, wherein the active agent is appropriate for chelating at least one metal and/or radionuclide.

BRIEF DESCRIPTION OF THE FIGURES

FIG. 1: Liver (a) and skeletal (b) retentions of Pu (in % of administered Pu) in untreated rats and rats chronically treated by two daily deposits on the rectal mucosa of DTPA in reverse-micellar system at 3.6, 7.2 or 12.5 mg.ml$^{-1}$, corresponding respectively to cumulative DTPA doses of 44.3, 88.6 or 153.8 µmol.kg$^{-1}$, or by four daily deposits at 12.5 mg.ml$^{-1}$ corresponding to the cumulative DTPA dose of 307.6 µmol.kg$^{-1}$.

FIG. 2: Decrease in retention of Pu in liver (a) and bone (b) as a function of the administered DTPA cumulative dose. The decrease in retention is expressed in % of control (absence of treatment). The cumulative dose is expressed in $\log_{10}$, µmol/kg.

FIG. 3: Liver (a) and skeletal (b) retentions of Pu in untreated and treated rats. The chronic treatment starting from H+1, D+4 or D+7 post-contamination consists in four daily deposits on the rectal mucosa of DTPA in reverse-micellar system at 12.5 mg.ml$^{-1}$, yielding a cumulative DTPA dose of 307.6 µmol.kg$^{-1}$.

DETAILED DESCRIPTION OF THE INVENTION

A first object of the invention is a reverse-micellar system comprising at least an active agent, an acylglycerol, a sterol, lecithin, ethanol and water, for use in chelation and/or sequestering of at least one radionuclide and/or metal in a patient in need thereof.

Components of the Reverse-Micellar System

Acylglycerols

Acylglycerols used in the reverse-micellar system according to the invention can be isolated from the majority of animals, and more preferably plants.

Acylglycerols used according to the invention include mono-, di- and tri-acylglycerols of the following formula (I):

in which:
R$_1$ is an acyl residue of a linear or branched unsaturated fatty acid having between 14 and 24 carbon atoms;
R$_2$ is an acyl residue of a linear or branched unsaturated fatty acid having between 2 and 18 carbon atoms, or a hydrogen atom;
R$_3$ is an acyl residue of a linear or branched unsaturated fatty acid having between 14 and 24 carbon atoms, or a hydrogen atom.

According to a particular embodiment, R$_1$ or R$_3$, preferably only one of R$_1$ and R$_3$, in particular only R$_1$, represents an acyl residue of oleic acid (C18: 1[cis]-9).

According to a particular aspect, R$_2$ has 18 carbon atoms, preferably R$_2$ is an oleic acid residue (oleoyl group), one of its positional isomers with respect to the double bond (cis-6,7,9,11 and 13) or one of its iso-branched isomers.

According to another particular aspect, R$_1$ represents an oleoyl group.

According to another particular aspect, R$_3$ is a hydrogen atom.

According to another particular aspect, R$_2$ and R$_3$ are hydrogen atoms.

As a general rule, oil containing a high concentration of oleic acid will be chosen as a useful source of acylglycerols according to the invention. Such oil usually contains a high proportion of acylglycerols useful according to the invention.

According to a particular aspect of the invention, the preferred acylglycerols are glycerol 1-monooleate and glycerol 1,2 -dioleate.

A certain number of them, and more particularly those which are found to be the most active in the applications sought after, are also available commercially. For instance, glycerol monooleate 40 contains about 32 to 52% of monoacylglycerol, 30 to 50% of diacylglycerol, 5 to 20% of triacylglycerol and is pharmaceutically accepted (*European Pharmacopeia* (8$^{th}$ Edition), USP 25/NF20, and *Japanese Standard of food Additives*). Such product is for instance commercially available by Gattefosse Company under the name Peceol®. In particular, Peceol® may comprise around 45.3 wt % of monoacyl glycerol, around 44.5 wt % of diacylglycerol and around 8.6 wt % of triacyl glycerol (the acyl fraction of Peceol® is mainly made of oleoyl—usually around 80% of the acyl residue is oleoyl fraction).

According to the present description, the weight of acylgylcerol corresponds to the total weight of the mixture usually containing an acylglycerol, or a mixture of acylglycerols, with glycerol and fatty acids derived from said acylglycerol(s), such as Peceol® described above.

Acylglycerols are natural compounds, and may be extracted and/or derived from renewable vegetable sources. Their use is thus favoured in terms of biocompatibility Sterol The reverse-micellar system according to the invention comprises at least one sterol, preferably natural sterol, such as cholesterol or phytosterol (vegetable sterols). Sitosterol and cholesterol are the preferred sterols that can be present in a reverse-micellar system according to the invention. Preferably, the reverse-micellar system comprises sitosterol.

Sitosterol and cholesterol are commercially available. More particularly, commercial sitosterol, which is extracted from soya, can be used. In such a product, the sitosterol generally represents from 50 to 80% by weight of the product and is generally found in a mixture with campesterol and sitostanol in respective proportions in the order of 15% each. Commercial sitosterol, which is extracted from a variety of pine called tall oil, can also be used.

Lecithin

In the present invention, the term "lecithin" designates phosphatidylcholine.

Phosphatidylcholine is also known as 1,2-diacyl-glycero-3-phosphocholine or PtdCho. Phosphatidylcholine is composed of a choline, a phosphate group, a glycerol and two fatty acids. It is actually a group of molecules, wherein the fatty acid compositions varies from one molecule to another. Phosphatidylcholine may be obtained from commercial lecithin that contains phosphatidylcholine in weight fractions of 20 to 98%. The lecithin preferably used according to the invention is Epikuron 200® and contains phosphatidylcholine at a fraction of more than 90%. Preferably, the lecithin used according to the invention comprises more than 92% wt phosphatidylcholine.

Water

The water useful for the preparation of the reverse-micellar system according to the invention is preferably purified water.

Other Components

The reverse-micellar system according to the invention may comprise any type of additional components. As example of additional component, one can cite alcohols different from ethanol.

The reverse-micellar system according to the invention may comprise at least one alcohol in addition to ethanol as defined above. The alcohols that may be used according to the invention are preferably linear or branched mono-alcohols with two to four carbon atoms. Examples of alcohols are 1-propanol, 2-propanol, 2-methyl-1-propanol, isopropanol, and any mixture thereof Polyols that may be used according to the invention are preferably glycerol and propylene glycol.

The amounts of the components of the reverse-micellar system can be adapted by anyone of ordinary skill in the art depending on the desired properties for the system, such as visual appearance, viscosity, and/or concentration of active agent for instance.

In a preferred embodiment, the reverse-micellar system does not comprise liposomes.

In an embodiment of the invention, the amounts of the components of the reverse-micellar system are adjusted so that the reverse-micellar system is in the form of a gel. A gel is sufficiently viscous and/or sticky for not flowing and remaining in place when applied onto the skin or onto a mucosa. Alternatively, the reverse-micellar system may be in the form of a liquid. One of ordinary skill in the art can adapt the relative amounts of active agent, acylglycerol, sterol, lecithin, ethanol and water in the reverse-micellar system for obtaining a gel with the desired properties, such as visual appearance, viscosity, and/or concentration of active agent for instance.

Examples of amounts for the different components of the reverse-micellar systems are the following:

The reverse-micellar system may comprise from 1 to 37%, preferably from 1 to 30%, in particular from 5 to 20% lecithin.

The reverse-micellar system may comprise from 0.1 to 20%, preferably from 1 to 20%, in particular from 5 to 15% water.

The reverse-micellar system may comprise from 5 to 20%, preferably from 5 to 15% alcohols, including ethanol.

The reverse-micellar system may comprise from 0.82 to 4.5% sterol.

The reverse-micellar system may comprise from 30 to 90%, preferably from 50 to 90% acylglycerol.

Unless otherwise specified, the percentage values used in the present invention are weight percentages with respect to the total weight of the reverse-micellar system.

In the present invention, the term "reverse-micellar system" relates to a reverse-phase system comprising an aqueous phase dispersed in an oil phase. Preferably, the reverse-phase system comprises reverse or reverse swollen micelles, but these may be organized in higher ordered isotropic structures such as water-in-oil micro emulsion or anisotropic structures such as cubic, hexagonal, lamellar organizations.

Active Agents

In the present invention, the term "active agent" refers to a compound appropriate for chelating and/or sequestering at least one metal and/or radionuclide. Said compound may be hydrophilic, amphiphilic or hydrophobic. Preferably, the active agent is hydrophilic.

According to the present invention, "chelation" and derivatives of this term relate to the formation or presence of one or more, preferably two or more, separate coordinate bonds between a polydentate (multiple bonded) ligand and a single central atom.

The term "sequestering agent" and derivatives of this term relate to a substance that captures an ion from a solution system by forming a ring, which does not have the chemical reactions of the ion which is removed.

In an embodiment, the active agent is a compound that is known to be useful for decorporating at least one radionuclide and/or treating at least one metal intoxication. Such compounds are well-known in the art and many prior art documents disclose examples of such compounds. One may for instance refer to Varani et al. *Frontiers in Medicinal Chemistry* 2009, 4, 130 or to Flora et al. *Int. J. Environ. Res. Public Health* 2010, 7, 2745 for examples of metal chelating and/or sequestering agents appropriate for chelating metals.

The reverse-micellar system of the invention is appropriate for encapsulating any active agent according to the present invention, whatever its physical-chemical parameters, such as molecular weight, chemical structure and/or charge. One of ordinary skill in the art will be able to adapt the ratios of the components of the reverse-micellar system and the amount of active agent to encapsulate any active agent into the reverse-micellar system according to the invention.

In an embodiment, the active agent is selected from the group consisting of DTPA, bisphosphonates (such as tiludronate, etidronate, or salt thereof), Prussian blue, EDTA, Trientine, D-penicillamine, Deferoxamine, BAL, DMSA, DMPS, Phytic acid, hydroxypyridonates (HOPO), mercaptoacetyltriglycine (MAG3) or chelating peptides, derivatives thereof and combinations thereof Derivatives of the cited compounds include esters or salts thereof, such as mesylate, calcium, sodium, or zinc.

A chelating peptide is according to the invention a natural or synthetic peptide, which is able to chelate and/or sequester at least one radionuclide and/or metal. Said chelating peptides mimic either the active site or the metal-binding site of at least one metalloprotein. Examples of peptides appropriate for chelating metals are disclosed in WO 2011/145055, Pujol et al. 2009, Pujol et al. 2011, Morris et al. 2013 and Zhang et al. 2013.

In particular, the active agent is a salt of DTPA, such as the calcium or zinc salt of DTPA. In particular, the active agent is pentetate calcium trisodium ($CaNa_3DTPA$).

The term "decorporation" is used in the present invention in relation with a radionuclide to refer to the elimination of at least some of said radionuclide from the patient body.

The term "agent for treating metal intoxication" refers in the present invention to a compound appropriate for chelating and preferably favor excretion of at least part of the metal comprised in the patient's body. Said metal may come for instance from an external intoxication (exposure to a metal) or to a pathology triggering metal accumulation in the body.

In an embodiment, the reverse-micellar system for use according to the invention is used for decorporating at least one radionuclide and/or treating at least one metal intoxication from the patient body. In this embodiment, decorporation or treatment of intoxication comprises the chelation and/or sequestering of the metal and/or radionuclide with a reverse-micelle system according to the invention and the elimination and/or excretion of the chelated and/or sequestered metal or radionuclide from the patient's body. In a preferred embodiment, the excretion is through natural routes, such as by urine or feces.

In an embodiment, the reverse-micellar system for use according to the invention is used for decorporating at least one radionuclide and/or treating at least one metal intoxication from an external lesion of the body. In this embodiment, decorporation or treating of the metal intoxication comprises the chelation and/or sequestering of the metal and/or radionuclide with a reverse-micelle system according to the invention and the elimination of the chelated and/or sequestered metal and/or radionuclide from the lesion, preferably by removal and/or washing. For instance, when the reverse-micellar system is applied as a gel on the lesion, the elimination can be performed by simple removal of the gel after chelation and/or sequestering of the radionuclide and/or metal.

DTPA is known to be appropriate for chelating plutonium, americium, curium, iron, californium, cerium, lanthanum, manganese and/or gallium. Bisphosphonates are known to be appropriate for chelating uranium. Prussian blue is known to be appropriate for chelating cesium and/or thallium. EDTA is known to be appropriate for chelating lead, manganese, cadmium and/or zinc. Trientine is known to be appropriate for chelating copper. D-penicillamine is known to be appropriate for chelating copper, lead, gold, mercury and/or zinc. Deferoxamine is known to be appropriate for chelating iron and/or aluminium. BAL is known to be appropriate for chelating lead, gold, mercury and/or arsenic. DMSA is known to be appropriate for chelating lead, mercury, arsenic, copper and/or antimony. DMPS is known to be appropriate for chelating lead, mercury, arsenic, and/or copper. Phytic acid is known to be appropriate for chelating uranium. Hydroxypyridonates (HOPO) are known to be appropriate for chelating plutonium, americium, uranium and/or neptunium, depending on members of HOPO. MAG3 is known for chelating technetium 99m. Peptides are known for chelating, not always exclusively, arsenic, cadmium, calcium, chromium, cobalt, copper, iron, lead, magnesium, mercury, molybdenum, nickel, silver, selenium, tellurium, thallium, tungsten, and/or zinc.

Radionuclides

The term "radionuclide", or radioactive nuclide, refers to an atom with an unstable nucleus, characterized by excess energy available to be imparted either to a newly created radiation particle within the nucleus or via internal conversion. During this process, the radionuclide is said to undergo radioactive decay, resulting in the emission of gamma ray(s) and/or subatomic particles such as alpha or beta particles.

In function of the active agent comprised in the reverse-micellar system, said system is appropriate for decorporation of any type of radionuclide. When the radionuclide is a specific isotope of an element, the reverse-micellar system will not necessarily more selectively chelate the radioactive isotope than the other isotopes of the same element.

In embodiments, the radionuclide is selected from the group consisting of plutonium, for instance $^{238}Pu$, $^{239}Pu$ or $^{240}Pu$, americium, for instance $^{241}Am$, uranium, for instance $^{233}U$, $^{234}U$, $^{235}U$, or $^{238}U$, cesium, for instance $^{134}Cs$, $^{135}Cs$ or $^{137}Cs$, thallium, for instance $^{201}Tl$ or $^{204}Tl$, indium, for instance $^{111}In$, strontium, for instance $^{85}Sr$, $^{89}Sr$ or $^{90}Sr$, molybdenum, for instance $^{99}Mo$ or $^{100}Mo$, lead, for instance $^{210}Pb$, chromium, for instance $^{51}Cr$, polonium, for instance $^{210}Po$, cobalt, for instance $^{57}Co$, $^{58}Co$ or $^{60}Co$, copper, for instance $^{64}Cu$ or $^{67}Cu$, gallium, for instance $^{67}Ga$, technetium, for instance $^{99m}Tc$, and degradation products thereof.

In an embodiment, the radionuclide is used in nuclear medicine.

In an embodiment, the radionuclide is used in at least one of nuclear power plants and armament.

The selectivity of the reverse-micellar system according to the invention for chelating or sequestering the radionuclides and/or metals is linked to the selectivity of the active agent comprised therein.

Metal

The metal that can be chelated and/or sequestered in the reverse-micellar system according to the invention may be any metal. For instance, the metal can be a transition metal, a heavy metal, a lanthanide or an alkali metal.

In an embodiment, the metal is selected from iron, aluminum, mercury, lead, arsenic, cadmium, copper, gold, beryllium, bismuth, cobalt, chromium, nickel, protactinium, polonium, silver, platinum, antimony, selenium, tin, technetium, titanium, zinc, manganese, and thallium. In another embodiment, the metal is gadolinium.

The terms "radionuclides" and "metals" refer in the present invention to any chemical form of said radionuclides and metals. For instance, the radionuclides and/or metals to be chelated according to the present invention may be in ionic form, optionally with at least one counter-ion or complexed with at least one other ligand, solvated or in the form of an oxide, before being chelated.

Decorporation and Treatment

In the present invention, the terms treatment or decorporation refer to any preventive and/or curative action that is capable of suppressing or decreasing the duration or intensity of any symptom due to the exposure to the radionuclide and/or metal, or In an embodiment, the metal or radionuclide is toxic for the patient, or the amount of said metal or radionuclide present in the patient in need of the treatment is toxic.

In an embodiment, the reverse-micellar system for use according to the invention is used in the treatment of at least one pathology linked to the accumulation and/or overload of at least one metal in a patient in need thereof.

An overload refers to a concentration of said metal in the patient body or in a specific organ or type of cells of the patient body higher than the recommended concentration for the maintenance of good health. In specific embodiments, the concentration is more than 2 times, more than 3 times, more than 5 times, more than 10 times, more than 50 times or more than 100 times higher than the recommended concentration. The recommended concentration may be dependent on different parameters, such as the sex or the age of the patient.

The pathology linked to the accumulation of at least one metal may be either a pathology leading to said accumulation, such as Wilson's disease or haemochromatosis, or a pathology or symptom due to an accumulation from an external origin. For instance, the accumulation may be due to a poisoning, preferably an unintentional poisoning of the patient with said metal. The poisoning may be due to ingestion or inhalation of said metal by the patient.

Wilson's disease or hepatolenticular degeneration is an autosomal recessive genetic disorder in which copper accumulates in tissues; this manifests as neurological or psychiatric symptoms and liver disease.

Mercury overload may be associated for instance with anxiety, memory loss, depression, suicidal tendencies, loss of strength and coordination, bleeding gums and tooth loss, abdominal cramps, diarrhea or chronic constipation, abnormal heart rate or blood pressure, repeated infections or cancer, chronic migraines, allergies, dermatitis, heart palpitations, sinus congestion, loss of appetite, chronic obesity and Alzheimer's disease.

Lead overload may be associated for instance with abdominal pain, hypertension, kidney problems, loss of appetite, fatigue, insomnia, hallucinations, headaches, tremors, arthritis, dizziness, mental retardation, autism, psychosis, allergies, dyslexia, hyperactivity, muscle weakness and paralysis.

Aluminium overload may be associated for instance with memory loss, learning difficulties, loss of coordination and orientation, mental confusion, colic, "heartburn", flatulence and headaches.

Arsenic overload may be associated for instance with nervous and sensory changes (numbness, tingling), burning sensations in the hands and feet, and progressive neuropathy (loss of nerve function).

Cadmium overload may be associated with obstructive lung disease, kidney disease, fragile bones, partial or total hair loss, anemia, arthritis, learning difficulties, headaches, growth retardation, osteoporosis, emphysema, loss of taste, smell, frighten, and cardiovascular diseases.

Chromium overload may be associated with lung cancer, asthma attacks in sensitive persons, stomach upsets and ulcers, convulsions, kidney and liver damages and allergic manifestations.

Iron overload (haemochromatosis, hemosiderosis, polycythemia, and iron-loading anemias) may be associated with cirrhosis of the liver, diabetes, cancer, cardiomyopathy, tanning of the skin, arthritis (iron deposition in joints), joint pain and bone pain.

Thallium overload may be associated with alopecia, memory loss, ataxia and tremors.

In an embodiment, the pathology is linked to the accumulation of at least one metal in at least one of liver, kidneys, bowel, brain, nervous system, spleen and eye.

In another embodiment, reducing metal levels may be necessary in neurologic pathologies in which some metals may synergize the disease. This is the case for instance of Alzheimer disease in which metal ions have been shown to increase the β-amyloid plaque aggregation.

Another object of the present invention is a reverse-micellar system comprising at least an active agent, an acylglycerol, a sterol, lecithin, ethanol and water, wherein the active agent is selected from the group consisting of DTPA, bisphosphonates, Prussian blue, EDTA, Trientine, D-penicillamine, Deferoxamine, BAL, DMSA, DMPS, Phytic acid, hydroxypyridonates (HOPO), mercaptoacetyltriglycine (MAG3) or chelating peptides, or derivatives thereof and combinations thereof.

In an embodiment, the reverse-micellar system for use according to the invention is used in the reduction of the cumulative radiation dose delivered to the tissues by internalized radionuclides. Indeed, the only possibility is decorporation of radionuclides by chelation, as to facilitate their excretion by natural means, such as urines or feces. According to a specific embodiment, the reverse-micellar system of the invention is for use in the reduction of the risk of developing diseases due to the cumulative radiation dose delivered to the tissues by radionuclides.

According to a specific embodiment, the reverse-micellar system of the invention is for use in the treatment of at least one disease linked to the accumulation and/or overload of at least one radionuclide in a patient in need thereof.

The diseases (or pathologies) linked to the accumulation and/or overload of at least one radionuclide may vary depending on the radiation exposure (duration and/or amount), it can include gastrointestinal disorders, such as nausea or vomiting, symptoms related to falling blood counts, such as predisposition to infection or bleeding, neurological disorders, or different types of cancers (such as blood cancers or thyroid cancer).

Exposure to radionuclides and thus accumulation and/or overload of radionuclides may have different origins, from the involvement of a nuclear worker after breaking of the containment of a glove box for example, to that of a multitude of people contaminated by the widespread dissemination of radionuclides in the environment, such as: incident/accident or natural disaster affecting facilities of research, production, operation or storage of nuclear materials, military conflict with nuclear weapons, radionuclide containing weapons, terrorist act aiming at these facilities or characterized by an explosive device dispersing radionuclides called "dirty bomb."

Internalized radionuclides are highly toxic and may cause both acute and chronic radiation injuries. The nuclides the most frequently encountered in these scenarios include actinides/lanthanides, such as americium, cesium, iodine, plutonium, strontium, or uranium. Once internalized in the body, the nuclide is distributed in several tissues (e.g. the lungs, bone and/or liver).

According to a particular embodiment, the treatment for actinide/lanthanide decorporation, such as Pu decorporation, is chelator diethylene triaminopentaacetic acid (DTPA).

Another object of the present invention is a reverse-micellar system comprising at least an active agent, an acylglycerol, a sterol, lecithin, ethanol, water, and at least one radionuclide and/or metal, wherein the at least one active agent is a compound appropriate for chelating and/or sequestering said radionuclide and/or metal.

The reverse-micellar system comprising at least one active agent and at least one radionuclide and/or metal according to the invention may be advantageously used for the delivery of the radionuclide and/or metal chelated and/or sequestered by the active agent to a patient.

Another object of the invention is a reverse-micellar system comprising at least an active agent, an acylglycerol, a sterol, lecithin, ethanol, water and a radionuclide and/or metal, wherein the active agent is a compound appropriate for chelating and/or sequestering said radionuclide and/or metal, for use as an imaging agent and/or as a Another object of the invention is a method of imaging at least part of at least one organ of a patient, comprising the administration of a reverse-micellar system comprising at least an active agent, an acylglycerol, a sterol, lecithin, ethanol, water and a radionuclide and/or metal, wherein the active agent is a compound appropriate for chelating and/or sequestering said radionuclide and/or metal. Said method of imaging advantageously further comprises a step of detecting the emitted radiation and/or signal, and preferably a step of forming an image therefrom.

Another object of the invention is the use of a reverse-micellar system comprising at least an active agent, an acylglycerol, a sterol, lecithin, ethanol, water and a radionuclide and/or metal, wherein the active agent is a compound appropriate for chelating and/or sequestering said radionuclide and/or metal, in the preparation of a composition to be used in a method of imaging and/or diagnosis.

The amount of reverse-micellar system to be administered for implementing the imaging method can be easily adapted by anyone of ordinary skill in the art in function of the amount of radionuclide and/or metal in the reverse-micellar system, the area(s) to visualize with this imaging method, and the imaging technique used.

The method of imaging may be for instance scintigraphy or Magnetic Resonance Imaging (MRI). In an embodiment, the method of imaging is scintigraphy of bone, kidney, brain and/or lung. The term "imaging agent" refers in the present invention to an agent that can be advantageously used in a method of imaging to improve the quantity and/or quality of the emitted radiation and/or signal or of the image formed therefrom.

Another object of the invention is thus a reverse-micellar system for use as an imaging agent according to the invention, wherein the imaging agent is used in scintigraphy and/or MRI.

The imaging agent may also be used for studying the perfusion of the renal and/or urinary tract function, or for determining the glomerular filtration rate.

The method of imaging according to the invention may be part of a diagnosis method for determining pathology, preferably pathology of the visualized area, for instance bone, kidney, brain and/or lung pathology. The term "diagnosis agent" refers in the present invention to an agent that can be advantageously used to help determining the existence of a pathology or of a risk of pathology, for instance a pathology of the bones, kidneys, brain and/or lungs.

In particular, the radionuclide comprised in the reverse-micellar system is technetium 99m, and/or the active agent is selected from the group consisting of bisphosphonates, DMSA, DTPA and mercaptoacetyltriglycine (MAG3). In that context, the radionuclide (such as technetium) with the active agent is in the form of a complex or chelate in the reverse-micellar system (such as Technetium ($^{99m}$Tc)-exametazime, Technetium (99mTc)-sestamibi, Technetium ($^{99m}$Tc)-DTPA, or Technetium ($^{99m}$Tc)-MAG3).

In particular, the metal comprised in the reverse-micellar system is gadolinium, and/or the active agent is DTPA. In that context, the metal with the active agent is in the form of a metal-based contrast agent (such as a gadolinium-based contrast agent) in the reverse-micellar system (such as Gd-HP-DO3A—also named as Gadoteridol-, Gd-DTPA Gd-DTPA-BMEA, Gd-EOB-DTPA, Gd-DOTA, or Gd-BOPTA).

The administration of the radionuclide and/or metal in the form of a chelate with the active agent allows first that the radionuclide and/or metal has no biological action in the organism, for instance it does not settle in the tissues, and second it affords an easy elimination of the radionuclide and/or metal after imaging. In addition, the reverse-micellar system affords an efficient delivery of the chelated and/or sequestered radionuclide and/or metal via the transmucosal route, which highly favors patient's compliance. In addition, the reverse-micellar system is appropriate for efficiently delivering the chelated and/or sequestered radionuclide and/or metal to any part of the body, such as bone, kidney, brain and/or lung with the same transmucosal administration route.

Comparatively, the administration of chelated technetium 99m is nowadays performed intravenously for bone, kidney and/or brain scintigraphy, but said chelated radionuclide is administered by inhalation in the form of an aerosol for lung scintigraphy.

The administration of chelated gadolinium for MRI is classically performed intravenously.

Administration of the Reverse-micellar Systems

The reverse micellar-systems according to the invention are able to be absorbed through mucosa and to vectorize active agents under a protected form to any tissue of the organism.

The reverse-micellar system may be administered via different routes. In a preferred embodiment of the invention, the reverse-micellar system is administered by topical or transmucosal route, preferably via transmucosal route.

As used herein, the terms "mucosa" and "mucosal" refer to a mucous tissue such as of the respiratory, digestive, or genital tissue. "Transmucosal delivery", "mucosal delivery", "mucosal administration" and analogous terms as used herein refer to the administration of a composition through a mucosal tissue. "Transmucosal delivery", "mucosal delivery", "mucosal administration" and analogous terms include, but are not limited to, the delivery of a composition through bronchi, gingival, lingual, nasal, oral, buccal, oesophageal, vaginal, rectal, and gastro-intestinal mucosal tissue.

In a specific embodiment, the mucosal administration is through buccal mucosal tissue.

The reverse-micellar system can be administered according to the invention at any time with respect to the exposure to and/or contamination with metal and/or radionuclide.

In an embodiment, the reverse-micellar system is administered preventively, that means before the exposure to and/or contamination with the radionuclide(s) and/or metal(s).

In another embodiment, the reverse-micellar system is administered in the first day, preferably in the first hour, in particular in the first 20 minutes, following the exposure to and/or contamination with the radionuclide(s) and/or metal(s).

In another embodiment, the reverse-micellar system is administered more than 24 hours, preferably more than 48 hours, in particular more than 96 hours, after the end of the exposure to the radionuclide(s) and/or metal(s).

The reverse-micellar system of the invention has been shown to be effective at decorporating a radionuclide when the treatment is started immediately after 1 hour, 4 days after, and even 7 days after the contamination, preferably the internal contamination.

The skilled practitioner will be able to adapt the number of daily administrations, the amount to be administered, the frequency of administration and/or the moment when the treatment is started in function of the amount of active agent present in the reverse-micellar system and the type and intensity of the contamination with the metal or radionuclide.

In the embodiment where the reverse-micellar system is used in the treatment of a pathology linked to the accumulation of at least one metal in a patient in need thereof, the pathology is not necessarily initiated by exposure to said metal. The pathology may also be linked to chronic exposure to a metal.

The reverse-micellar system may be formulated in a composition further comprising a pharmaceutically acceptable support.

Another object of the invention is a pharmaceutical composition comprising a pharmaceutically acceptable support and a reverse-micellar system comprising at least an active agent, an acylglycerol, lecithin, ethanol and water, wherein the active agent is a compound appropriate for chelating and/or sequestering at least one metal and/or radionuclide.

The term "pharmaceutically acceptable support" refers to any pharmaceutically acceptable excipient, vehicle or carrier, well-known to the person skilled in the art. Other additives well-known to the person skilled in the art such as stabilisers, drying agents, binders or pH buffers may also be used. Preferred excipients in accordance with the invention promote adherence of the finished product to the mucosa.

According to particular embodiments, the pharmaceutical composition is in the form of a capsule, a caplet, an aerosol, a spray, a solution or a soft elastic gelatin capsule.

In an embodiment, the reverse-micellar system comprised in the pharmaceutical composition further comprises at least one radionuclide and/or metal, and the at least one active agent comprised in the reverse-micellar system is a compound appropriate for chelating and/or sequestering said radionuclide and/or metal.

Preparation of the Reverse-Micellar Systems of the Invention

The reverse-micellar systems of the invention may be prepared by any technique known in the art. They are more particularly obtainable by the following method:

(a) Contacting (i) acylglycerol, preferably diacylglycerol, (ii) lecithin, (iii) ethanol, (iv) water, preferably purified water, (v) sterol, and (vi) at least one active agent, (b) Stirring mixture obtained in step (a), at 40° C. or less, and for a time sufficient to obtain formation of the reverse-micellar system.

The parameters of stirring, for instance duration and speed of mechanical stirring, can be readily determined by any one skilled in the art and depend on experimental conditions. In practice, these parameters are such that a homogenous reverse-micellar system is obtained; the speed is determined so as to enable formation of a visually limpid formulation, and duration of the stirring is such that the stirring may be stopped a few minutes after obtaining the visually limpid formulation.

In the embodiments where the reverse-micellar system further comprises a radionuclide and/or metal, said radionuclide and/or metal is preferably introduced in the system at step (a).

The following examples are provided as illustrative, and not limitative, of the present invention.

EXAMPLES

Example 1

Reverse-micellar Systems Comprising $CaNa_3DTPA$

Sample A 35.7 g of commercially available lecithin, containing more than 90% of phosphatidylcholine were dissolved in 21.5 g of absolute ethanol under magnetic stirring at 300 r/min at room temperature. 5.9 g of phytosterol, containing more than 70% of beta-sitosterol, were added to the mixture and stirred in the same conditions. 144.6 g of Peceol® were added thereto and magnetic stirring was carried out at 700 r/min at 37° C. to form an oil mixture.

6.0 g of a solution containing 647.9 mg of $CaNa_3DTPA$ in water were added to 41.5 g of the oil mixture at room temperature. 2.0 g of absolute ethanol were then added to the mixture by vortexing few minutes to form microemulsion containing 13.1 mg/g or 12.5 mg/ml of $CaNa_3DTPA$ (density of 0.95).

Sample B 3.0 g of a solution containing 187.6 mg of $CaNa_3DTPA$ in water were added at room temperature to 20.7 g of the oil mixture prepared for the sample A formulation. 1.0 g of absolute ethanol were then added to the mixture by vortexing few minutes to form microemulsion containing 7.6 mg/g or 7.2 mg/ml of $CaNa_3DTPA$ (density of 0.95).

Sample C 3.0 g of a solution containing 95.1 mg of $CaNa_3DTPA$ in water were added at room temperature to 20.7 g of the oil mixture prepared for the sample A formulation. 1.0 g of absolute ethanol were then added to the mixture by vortexing few minutes to form microemulsion containing 3.8 mg/g or 3.6 mg/ml of $CaNa_3DTPA$ (density of 0.95).

Sample D 21.4 g of commercially available lecithin, containing more than 90% of phosphatidylcholine were dissolved in 12.8 g of absolute ethanol under magnetic stirring at 300 r/min at room temperature. 3.6 g of phytosterol, containing more than 70% of beta-sitosterol, were added to the mixture and stirred in the same conditions. 86.8 g of Peceol® were added thereto and magnetic stirring was carried out at 700 r/min at 37° C. to form an oil mixture.

12.1 g of a solution containing 1.3 g of $CaNa_3DTPA$ in water were added to 83.0 g of the oil mixture at room temperature. 4.0 g of absolute ethanol were then added to the mixture by vortexing few minutes to form microemulsion containing 13.1 mg/g or 12.5 mg/ml of $CaNa_3DTPA$ (density of 0.95).

Examples 2-4

Materials and Methods

The animals used were male rats of the Sprague-Dawley strain of about 8 weeks of age upon arrival in the laboratory. Four to five rats form a test batch.

Under gaseous isoflurane anesthesia, each rat received an injection in a tail vein of 200 µl of a citrate solution of plutonium (9703-9778 Bq; composition: 99.4% $^{238}Pu$+0.4% $^{239}Pu$+0.2% $^{241}Am$ (alpha activity), pH 6.5, 2 to 6.8 mM citrate).

The active agent is $CaNa_3DTPA$, being the trisodium calcium salt form of the chelating agent DTPA, incorporated into the reverse-micellar system according to the invention.

Using a micropipette and its cut blunt cone, each rat of the treated groups received an intrarectal administration of 200 µl of reverse-micelle composition comprising $CaNa_3DTPA$ (3.6, 7.2 or 12.5 mg $CaNa_3DTPA$/ml reverse-micelles), at 2 or 4 times daily for 5 consecutive days. This chronic repeated administration protocol begins 1 hour (H+1), 4 days (D+4) or 7 days (D+7) after contamination. For implementing the treatment, the rats were made slightly sleepy with gaseous isoflurane anesthesia to ensure a more reproducible deposition. Just before the deposition on the rectal mucosa, feces that may be present in the rat rectum are removed mechanically by palpation. Despite this precaution, the introduction of the cone into the rectum can stimulate defecation. If this takes place immediately after deposition (<few seconds), a second deposit is made.

Euthanasia and tissue samples: Under deep pentobarbital anesthesia, the rats are euthanized 12-14 days after the contamination, by laparotomy, a section of the abdominal aorta and the diaphragm. Liver and both femurs were removed.

Mineralization of biological samples: Tissue samples were calcined in the oven and then mineralized in wet conditions ($H_2O_2$+$HNO_3$ 2N). Mineralized samples are then dissolved in 2N $HNO_3$.

Physical measurements of alpha activity: The content of alpha activity of each sample was measured by liquid scintillation counting.

Example 2

Chronic Treatment with $CaNa_3$-DTPA Incorporated in a Reverse-micellar System According to the Invention Four days after the Pu contamination, rats followed a chronic treatment protocol consisting of two rectal administrations of the reverse-micellar system comprising DTPA daily for 5 days, each deposit being done at 3.6, 7.2 or 12.5 mg $CaNa_3DTPA.ml^{-1}$ in reverse-micellar system, leading to cumulative doses of 44.3, 88.6 or 153.8 µmol.$kg^{-1}$ (samples A, B and C), or in 4 daily rectal deposits at 12.5 mg.$ml^{-1}$, leading to the cumulative DTPA dose of 307.6 µmol.$kg^{-1}$ (sample A).

Figure 1A:
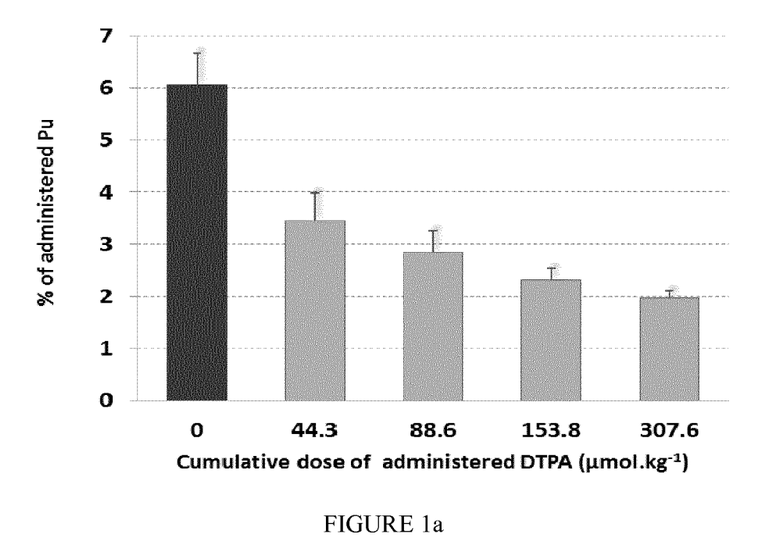
Figure 1B:
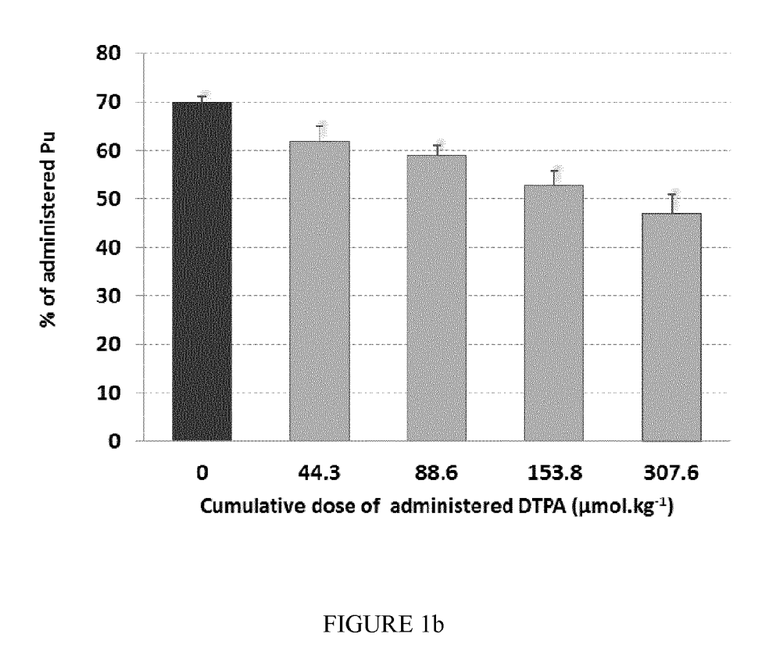

At D+12 to 14, the liver and bone retention of Pu were lower for treated rats than those of the untreated control rats (see FIGS. 1a and 1b). Chronic treatment with the reverse-micellar system comprising $CaNa_3DTPA$ is therefore efficient for decorporating Pu.

Figure 2A:
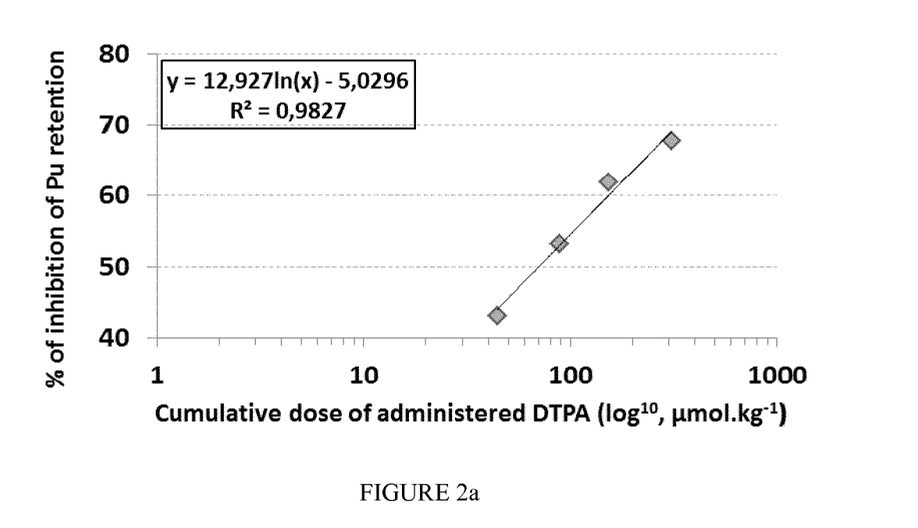
Figure 2B:
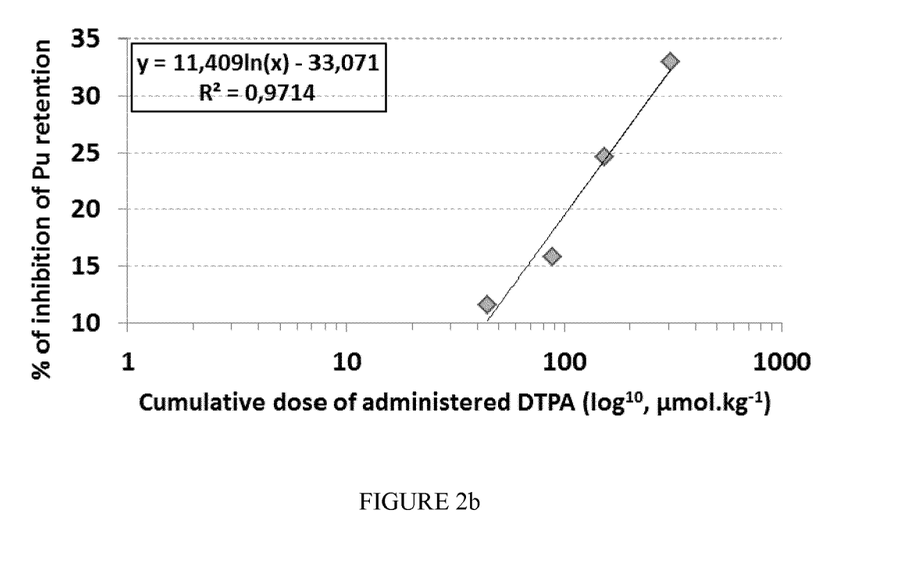

The efficacy of decorporation in liver or bone Pu deposits is proportional to the administered dose cumulative of $CaNa_3DTPA$ (see FIGS. 2a and 2b).

Example 3

Influence of the Moment of the Initiation of the Treatment

One hour, four days or seven days after the Pu contamination, rats followed a chronic treatment protocol consisting in 4 rectal administrations of the reverse micellar system comprising $CaNa_3DTPA$ daily for 5 days, each deposit being done at 12.5 mg $CaNa_3DTPA$ per ml of reverse-micellar system, leading to a cumulative dose of 307.6 µmol.$kg^{-1}$ (sample D). On D+12 to 14, treated rats have lower liver and bone deposits of Pu than those of untreated control rats, regardless of the time of initiation of chronic treatment protocol (see FIGS. 3a and 3b).

Figure 3A:
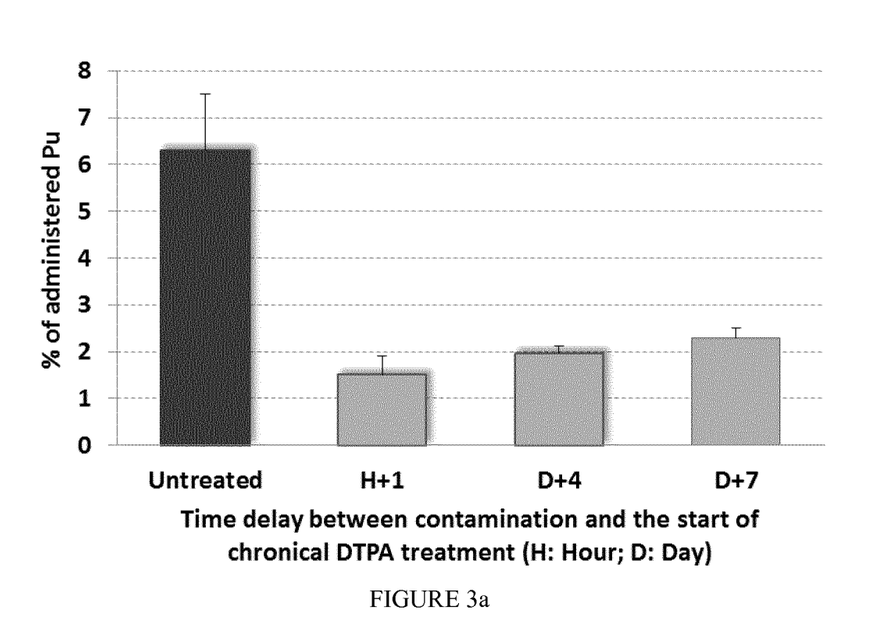
Figure 3B:
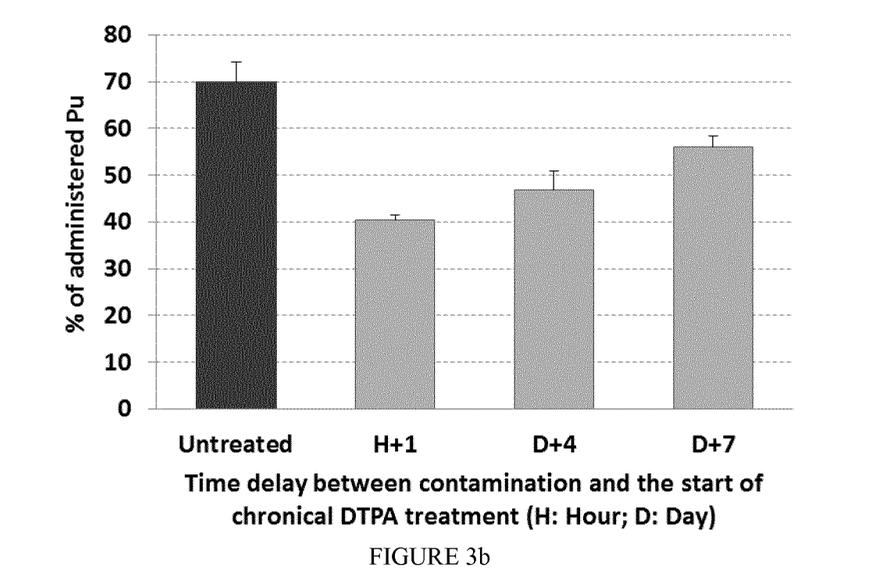

This decorporation of systemic Pu deposits in liver and bone by a protocol of chronic treatment with the reverse-micellar system comprising $CaNa_3DTPA$ is more effective if the protocol begins early after Pu contamination (see FIGS. 3a and 3b).

Example 4

Influence of the Frequency of Rectal Deposits on the Efficacy of the Treatment

The cumulative doses of 44.3, 88.6 and 153.8 µmol.$kg^{-1}$ $CaNa_3DTPA$ result from two daily administrations for 5 days of 3.6, 7.2 and 12.5 mg of $CaNa_3DTPA$ per ml of reverse-micellar system (samples A, B and C). The cumulative dose of 307.6 µmol.$kg^{-1}$ $CaNa_3DTPA$ results from 4 daily administrations for 5 days of 12.5 mg of $CaNa_3DTPA$ per ml of reverse micellar system (sample A). The point corresponding to the efficacy of decorporation of the Pu deposits for the cumulative dose of 307.6 µmol.$kg^{-1}$ aligns with the linear regression performed for lower cumulative doses (see FIGS. 1 and 2).

This strongly suggests the absence of influence of daily dosing frequency on the efficacy of chronic treatment protocol, the dosage seeming to be the determining factor for the effectiveness of the chronic protocol in the range of dosages tested.

Examples 2-4, Conclusions

The overall results show the effectiveness of $CaNa_3DTPA$ incorporated in the reverse-micellar system for decorporating systemic and tissue Pu deposits.

The undeniable advantage of this dosage form is its potential for simple, fast and autonomous administration, including making repeated undemanding treatment. As the chemical structure of $CaNa_3DTPA$ is not altered by the formulation, any element for which the $CaNa_3DTPA$ is recommended or suspected to be effective could also be formulated similarly.

Example 5

Reverse-micellar Systems Comprising PEG-amine Stabilized Nanoparticles of ferric hexacyanoferrate (II) (Prussian Blue)

Sample E 7.1 g of commercially available lecithin, containing more than 90% of phosphatidylcholine were dissolved in 4.3 g of absolute ethanol under magnetic stirring at 300 r/min at room temperature. 1.2 g of phytosterol, containing more than 70% of beta-sitosterol, were added to the mixture and stirred in the same conditions. 28.9 g of Peceol® were added thereto and magnetic stirring was carried out at 700 r/min and 37° C. to form an oil mixture.

244.7 mg of a solution containing 4.1 mg PEG-amine stabilized nanoparticles of prussian blue in water were mixed with 1.7 g of the oil mixture by vortexing a few minutes to form a microemulsion containing 2.1 mg/g or 2.0 mg/ml of PEG-amine stabilized nanoparticles of prussian blue (density of 0.95).

Sample F 3.8 g of commercially available lecithin, containing more than 90% of phosphatidylcholine were dissolved in 2.3 g of absolute ethanol under magnetic stirring at 300 r/min and room temperature. 0.5 g of phytosterol, containing more than 70% of beta-sitosterol, were added to the mixture and stirred in the same conditions. 9.5 g of Peceol® were added thereto and magnetic stirring was carried out at 700 r/min and 37° C. to form an oil mixture.

297.2 mg of a solution containing 7.9 mg of PEG-amine stabilized nanoparticles of prussian blue in water were mixed with 1.6 g of the oil mixture by vortexing a few minutes to form a microemulsion containing 4.2 mg/g or 4.0 mg/ml of PEG-amine stabilized nanoparticles of prussian blue (density of 0.95).

Example 6

Reverse-micellar Systems Comprising tiludronate

Sample G 28.4 g of commercially available lecithin, containing more than 90% of phosphatidylcholine were dissolved in 17.1 g of absolute ethanol under magnetic stirring at 300 r/min and room temperature. 4.8 g of phytosterol, containing more than 70% of beta-sitosterol, were added to the mixture and stirred in the same conditions. 115.7 g of Peceol® were added thereto and magnetic stirring was carried out at 700 r/min and 37° C. to form an oil mixture.

120.3 mg of a solution containing 1.0 mg of tiludronate in water were mixed with 829.8 mg of the oil mixture by vortexing a few minutes to form a microemulsion containing 1.1 mg/g or 1.0 mg/ml of tiludronate (density of 0.95).

Sample H 19.0 g of commercially available lecithin, containing more than 90% of phosphatidylcholine were dissolved in 11.4 g of absolute ethanol under magnetic stirring at 300 r/min and room temperature. 2.4 g of phytosterol, containing more than 70% of beta-sitosterol, were added to the mixture and stirred in the same conditions. 47.2 g of Peceol® were added thereto and magnetic stirring was carried out at 700 r/min and 37° C. to form an oil mixture.

212.3 mg of a solution containing 8.3 mg of tiludronate in water were mixed with 1.4 g of the oil mixture by vortexing a few minutes to form a microemulsion containing 5.1 mg/g or 4.8 mg/ml of tiludronate (density of 0.95).

Example 7

Reverse-micellar Systems Comprising $CaNa_3DTPA$

Sample I 56.4 g of commercially available lecithin, containing more than 90% of phosphatidylcholine were dissolved in 24.4 g of absolute ethanol under magnetic stirring at 300 r/min and room temperature. 4.7 g of phytosterol, containing more than 70% of beta-sitosterol, were added to the mixture and stirred in the same conditions. 62.5 g of Peceol® were added thereto and magnetic stirring was carried out at 700 r/min and 37° C. to form an oil mixture.

16.2 g of a solution containing 2.4 g of $CaNa_3DTPA$ in water were mixed with 59.9 g of the oil mixture by vortexing a few minutes to form a microemulsion containing 31.4 mg/g or 30.5 mg/ml of $CaNa_3DTPA$ (density of 0.97).

Sample J 28.5 g of commercially available lecithin, containing more than 90% of phosphatidylcholine were dissolved in 8.6 g of absolute ethanol under magnetic stirring at 300 r/min and room temperature. 2.4 g of phytosterol, containing more than 70% of beta-sitosterol, were added to the mixture and stirred in the same conditions. 35.6 g of Peceol® were added thereto and magnetic stirring was carried out at 700 r/min and 37° C. to form an oil mixture.

401.2 mg of a solution containing 4.1 mg of $CaNa_3DTPA$ in water were mixed with 1.5 g of the oil mixture by vortexing a few minutes to form a gel containing 2.1 mg/g of $CaNa_3DTPA$.

Example 8

Reverse-micellar Systems Comprising deferoxamine mesylate

Sample K 4.7 g of commercially available lecithin, containing more than 90% of phosphatidylcholine were dissolved in 8.6 g of absolute ethanol under magnetic stirring at 300 r/min and room temperature. 2.4 g of phytosterol, containing more than 70% of beta-sitosterol, were added to the mixture and stirred in the same conditions. 73.4 g of Peceol® were added thereto and magnetic stirring was carried out at 700 r/min and 37° C. to form an oil mixture.

119.8 mg of a solution containing 12.0 mg of deferoxamine mesylate in water were mixed with 1.8 g of the oil mixture by vortexing a few minutes to form a microemulsion containing 6.3 mg/g or 5.9 mg/ml of deferoxamine mesylate (density of 0.94).

Sample L 14.3 g of commercially available lecithin, containing more than 90% of phosphatidylcholine were dissolved in 8.6 g of absolute ethanol by magnetic stirring at 300 r/min and room temperature. 2.4 g of phytosterol, containing more than 70% of beta-sitosterol, were added to the mixture and stirred in the same conditions. 57.8 g of Peceol® were added thereto and magnetic stirring was carried out at 700 r/min and 37° C. to form an oil mixture.

239.8 mg of a solution containing 24.0 mg of deferoxamine mesylate in water were mixed with 1.7 g of the oil mixture by vortexing a few minutes to form a microemulsion Example 9

Reverse-micellar Systems Comprising $CaNa_2EDTA$

Sample M 301.3 mg of a solution containing 37.2 mg of $CaNa_2EDTA$ in water were mixed with 1.6 g of the oil mixture described in sample H formulation by vortexing a few minutes to form a microemulsion containing 19.4 mg/g or 18.4 mg/ml of $CaNa_2EDTA$ (density of 0.95).

Sample N 28.5 g of commercially available lecithin, containing more than 90% of phosphatidylcholine were dissolved in 11.4 g of absolute ethanol under magnetic stirring at 300 r/min and room temperature. 2.4 g of phytosterol, containing more than 70% of beta-sitosterol, were added to the mixture and stirred in the same conditions. 32.8 g of Peceol® were added thereto and magnetic stirring was carried out at 700 r/min and 37° C. to form an oil mixture.

400.8 mg of a solution containing 41.9 mg of $CaNa_2EDTA$ in water were mixed with 1.5 g of the oil mixture by vortexing a few minutes to form a microemulsion containing 22.0 mg/g or 21.1 mg/ml of $CaNa_2EDTA$ (density of 0.96).

Example 10

Reverse-micellar Systems Comprising D-penicillamine

Sample O 120.8 mg of a solution containing 10.2 mg of D-penicillamine in water were mixed with 1.8 g of the oil mixture described in sample K formulation by vortexing a few minutes to form a microemulsion containing 5.3 mg/g or 5.0 mg/ml of D-penicillamine (density of 0.94).

Sample P 244.9 mg of a solution containing 20.4 mg of D-penicillamine in water were mixed with 1.7 g of the oil mixture described in sample L formulation by vortexing a few minutes to form a microemulsion containing 10.5 mg/g or 10.0 mg/ml of D-penicillamine (density of 0.95).

Example 11

Reverse-micellar Systems Comprising trientine

Sample Q 120.0 mg of a solution containing 18.8 mg of trientine in water were mixed with 837.4 mg of the oil mixture described in sample L formulation by vortexing a few minutes to form a microemulsion containing 19.6 mg/g or 18.6 mg/ml of trientine (density of 0.95).

Example 12

Reverse-micellar Systems Comprising dimercaprol (BAL)

Sample R 11.8 mg of dimercaprol were mixed with 828.9 mg of the oil mixture described in sample L formulation and to 108 mg of water by vortexing a few minutes to form a microemulsion containing 12.4 mg/g or 11.8 mg/ml of dimercaprol (density of 0.95).

Sample S 118.5 mg of dimercaprol were mixed with 830.8 mg of the oil mixture described in sample L formulation by vortexing a few minutes to form a microemulsion containing 124.4 mg/g or 120.6 mg/ml of dimercaprol (density of 0.97).

Example 13

Reverse-micellar Systems Comprising phytic acid

Sample T 239.5 mg of a solution containing 10.0 mg of phytic acid in water were mixed with 1.7 g of the oil mixture described in sample L formulation by vortexing a few minutes to form a microemulsion containing 5.2 mg/g or 4.9 mg/ml of phytic acid (density of 0.95).

Sample U 400.0 mg of a solution containing 20.1 mg of phytic acid in water were mixed with 1.5 g of the oil mixture described in sample J by vortexing a few minutes to form a gel containing 10.5 mg/g of phytic acid.

Example 14

Reverse-micellar System Comprising etidronate disodium

Sample V 15.0 g of commercially available lecithin, containing more than 90% of phosphatidylcholine were dissolved in 9.0 g of absolute ethanol under magnetic stirring at 300 r/min and room temperature. 2.5 g of phytosterol, containing more than 70% of beta-sitosterol, were added to the mixture and stirred in the same conditions. 60.9 g of Peceol® were added thereto and magnetic stirring was carried out at 700 r/min and 37° C. to form an oil mixture.

5.1 g of a solution containing 72 mg of etidronate disodium in water were mixed with 34.9 g of the oil mixture by vortexing a few minutes to form a microemulsion containing 1.8 mg/g of etidronate disodium.

Example 15

Reverse-micellar System Comprising Gadolinium-DTPA (Gd-DTPA) Complex

Sample W 141.0 g of commercially available lecithin, containing more than 90% of phosphatidylcholine were dissolved in 122 g of absolute ethanol under magnetic stirring at 300 r/min and room temperature. 23.5 g of phytosterol, containing more than 70% of beta-sitosterol, were added to the mixture and stirred in the same conditions. 533.4 g of $P_{eceo}l$® were added thereto and magnetic stirring was carried out at 700 r/min and 37° C. to form an oil mixture.

240.8 mg of a solution containing 10.9 mg of Gd-DTPA in water were mixed with 1.7 g of the oil mixture by vortexing a few minutes to form a microemulsion containing 5.7 mg/g of Gd-DTPA.

Example 16

Reverse-micellar System Comprising Gadolinium-HP-DO3A (Gadoteridol) Complex

Sample X 34.9 g of commercially available lecithin, containing more than 90% of phosphatidylcholine were dissolved in 5.8 g of absolute ethanol under magnetic stirring at 300 r/min and room temperature. 30.2 g of phytosterol, containing more than 70% of beta-sitosterol, were added to the mixture and stirred in the same conditions. 131.8 g of Peceol® were added thereto and magnetic stirring was carried out at 700 r/min and 37° C. to form an oil mixture.

1.2 g of a solution containing 294.8 mg of Gadoteridol in water were mixed with 8.8 g of the oil mixture by vortexing a few minutes to form a microemulsion containing 29.5 mg/g of gadoteridol.

Table 1 shows the amounts (w/w %) of individual components in the different samples.

TABLE 1

| Samples | API (%) | Lecithin (%) | Phytosterol (%) | Ethanol (%) | Peceol (%) | Aqueous solution (%) |
|---|---|---|---|---|---|---|
| A | CaNa₃DTPA (1.31) | 14.4 | 2.4 | 12.7 | 58.3 | 12.2 |

TABLE 1-continued

| Samples | API (%) | Lecithin (%) | Phytosterol (%) | Ethanol (%) | Peceol (%) | Aqueous solution (%) |
|---|---|---|---|---|---|---|
| B | CaNa$_3$DTPA (0.76) | 14.4 | 2.4 | 12.7 | 58.3 | 12.2 |
| C | CaNa$_3$DTPA (0.38) | 14.4 | 2.4 | 12.7 | 58.3 | 12.2 |
| D | CaNa$_3$DTPA (1.31) | 14.4 | 2.4 | 12.7 | 58.3 | 12.2 |
| E | Prussian Blue (0.21) | 15.0 | 2.5 | 9.0 | 60.9 | 12.6 |
| F | Prussian Blue (0.42) | 19.9 | 2.5 | 12.0 | 49.8 | 15.8 |
| G | Tiludronate (0.11) | 15.0 | 2.5 | 9.0 | 60.9 | 12.6 |
| H | Tiludronate (0.51) | 20.0 | 2.5 | 12.0 | 49.7 | 15.8 |
| I | CaNa$_3$DTPA (3.14) | 30.0 | 2.5 | 13.0 | 33.2 | 21.3 |
| J | CaNa$_3$DTPA (0.21) | 30.0 | 2.5 | 9.0 | 37.5 | 21.0 |
| K | Deferoxamine mesylate (0.63) | 5.0 | 2.5 | 9.0 | 77.2 | 6.3 |
| L | Deferoxamine mesylate (1.26) | 15.0 | 2.5 | 9.0 | 60.9 | 12.6 |
| M | CaNa$_2$EDTA (1.94) | 20.0 | 2.5 | 12.0 | 49.7 | 15.8 |
| N | CaNa$_2$EDTA (2.20) | 30.0 | 2.5 | 12.0 | 34.5 | 21.0 |
| O | D-penicillamine (0.53) | 5.0 | 2.5 | 9.0 | 77.2 | 6.3 |
| P | D-penicillamine (1.05) | 15.0 | 2.5 | 9.0 | 60.7 | 12.8 |
| Q | Trientine (1.96) | 15.0 | 2.5 | 9.0 | 60.9 | 12.6 |
| R | Dimercaprol (1.24) | 15.0 | 2.5 | 9.0 | 60.8 | 11.4 |
| S | Dimercaprol (12.4) | 15.0 | 2.5 | 9.0 | 60.8 | 0.0 |
| T | Phytic acid (0.52) | 15.0 | 2.5 | 9.0 | 60.9 | 12.6 |
| U | Phytic acid (1.05) | 30.0 | 2.5 | 9.0 | 37.5 | 21.0 |
| V | Etidronate disodique (0.18) | 15.0 | 2.5 | 9.0 | 60.8 | 12.7 |
| W | Gd-DTPA (0.57) | 15.0 | 2.5 | 13.0 | 56.9 | 12.6 |
| X | Gd-HP-DO3A (2.95) | 15.0 | 2.5 | 13.0 | 57.2 | 12.0 |

The invention claimed is:

1. A reverse-micellar system comprising an active agent, an acylglycerol, a sterol, lecithin, ethanol and water, wherein the active agent chelates at least one metal, chelates at least one radionuclide, sequesters at least one metal, or sequesters at least one radionuclide; wherein the active agent consists of diethylene triaminopentaacetic acid (DTPA), bisphosphonates, Prussian blue, ethylene diamine tetraacetic acid (EDTA), trientine, D-penicillamine, deferoxamine, British anti-Lewisite (BAL), dimercaptosuccinic acid (DMSA), 2,3-dimercaptopropane-1-sulfonic acid (DMPS), phytic acid, hydroxypyridonates (HOPO), mercaptoacetyltriglycine (MAG3), derivatives thereof or combinations thereof.

2. The reverse-micellar system of claim 1, wherein the sterol is sitosterol.

3. A pharmaceutical composition comprising a pharmaceutically acceptable support and the reverse-micellar system of claim 1.

4. The reverse-micellar system of claim 1, wherein the active agent is pentetate calcium trisodium (CaNa$_3$ DTPA).

5. The reverse-micellar system of claim 1, wherein the active agent has a concentration of 1-124.4 mg/g.

* * * * *